US010829833B2

(12) United States Patent
Gos et al.

(10) Patent No.: US 10,829,833 B2
(45) Date of Patent: *Nov. 10, 2020

(54) BIOLOGICAL PROCESSING OF SCRAP METAL, HOUSEHOLD WASTE AND/OR INDUSTRIAL WASTE FOR THE ISOLATION OF HEAVY METALS

(71) Applicant: B.R.A.I.N. Biotechnology Research and Information Network AG, Zwingenberg (DE)

(72) Inventors: Stephen Gos, Miltenberg (DE); Andrea Christiansen, Rostock (DE); Xin Lu, Essen (DE); Guido Meurer, Seeheim-Jugenheim (DE); Yvonne Tiffert, Mannheim (DE); Esther Gabor, Zwingenberg (DE); Benedikt Hoffmann, Aschaffenburg (DE); Martin Langer, Karlsruhe (DE)

(73) Assignee: B.R.A.I.N. Biotechnology Research and Information Network AG, Zwingenberg (DE)

( * ) Notice: Subject to any disclaimer, the term of this patent is extended or adjusted under 35 U.S.C. 154(b) by 254 days.

This patent is subject to a terminal disclaimer.

(21) Appl. No.: 15/562,748

(22) PCT Filed: Mar. 30, 2016

(86) PCT No.: PCT/EP2016/056927
§ 371 (c)(1),
(2) Date: Sep. 28, 2017

(87) PCT Pub. No.: WO2016/156405
PCT Pub. Date: Oct. 6, 2016

(65) Prior Publication Data
US 2018/0073100 A1    Mar. 15, 2018

(30) Foreign Application Priority Data
Mar. 30, 2015  (EP) .................................. 15161646

(51) Int. Cl.
*C22B 3/24* (2006.01)
*C12N 1/20* (2006.01)
(Continued)

(52) U.S. Cl.
CPC .................. *C22B 3/24* (2013.01); *C12N 1/20* (2013.01); *C12N 1/22* (2013.01); *C12N 1/34* (2013.01);
(Continued)

(58) Field of Classification Search
None
See application file for complete search history.

(56) References Cited

U.S. PATENT DOCUMENTS 4,880,740 A    11/1989   Hoffmann et al.
5,007,620 A     4/1991   Emmett, Jr. et al.
(Continued)

FOREIGN PATENT DOCUMENTS

CA      2721235       10/2009
CN    103205381 B      5/2014
(Continued)

OTHER PUBLICATIONS

Auger et al., Appl. Environ. Microbio., 2009, 75:6616-6618 (Year: 2009).*
(Continued)

*Primary Examiner* — Allison M Fox
*Assistant Examiner* — Qing Xu
(74) *Attorney, Agent, or Firm* — David M. Saravitz; Williams Mullen

(57) ABSTRACT

The invention provides a process of isolating or enriching a heavy metal present in a liquid medium. The process comprising the following steps: (a) incubating a suspension containing (i) particulate scrap metal, household waste and/or industrial waste containing a heavy metal in elemental
(Continued)

form and (ii) biomass comprising a bacterium, or a combination of two or more bacteria, capable of binding the heavy metal; (b) separating the biomass having bound heavy metal from the suspension of step (a); and (c) isolating the heavy metal from the biomass separated in step (b).

19 Claims, 4 Drawing Sheets

(51) Int. Cl.
    *C12N 1/22* (2006.01)
    *C12N 1/34* (2006.01)
    *C22B 3/18* (2006.01)
    *C22B 3/00* (2006.01)

(52) U.S. Cl.
    CPC .............. *C22B 3/18* (2013.01); *C22B 11/042* (2013.01); *Y02P 10/234* (2015.11)

(56) References Cited

U.S. PATENT DOCUMENTS

| 5,162,105 | A | 11/1992 | Kleid et al. |
| 2001/0011376 | A1* | 8/2001 | Shannon ................ A01K 63/04 800/13 |
| 2012/0036962 | A1 | 2/2012 | Yun et al. |

FOREIGN PATENT DOCUMENTS

| EP | 0432935 A1 | 6/1991 |
| EP | 2813585 A1 | 12/2014 |
| WO | WO-2009/130006 A1 * | 10/2009 |

OTHER PUBLICATIONS

International Search Report and Written Opinion for PCT/EP2016/056927, EPO, dated Jun. 8, 2016.
Churchill, S.A., et al., "Sorption of heavy metals by prepared bacterial cell surfaces", Journal of Environmental Engineering, US, vol. 121, No. 10, pp. 706-711, Jan. 1, 1995.
Beveridge, T.J., et al., "Uptake and Retention of Metals by cell Walls of Bacillus subtilis", Journal of Bacteriology, vol. 127, No. 3, pp. 1502-1518, Sep. 1976.
Charley, Robert C., et al, "Bioaccumulation of Silver by a Multispecies Community of Bacteria", Archives of Microbiology 123, pp. 239-244 (1979).
Lengke, M. F.; Charoen Sanpawanitchakit & Gordon Southam, "Chapter 3: Biosynthesis of Gold Nanoparticles: A Review." Metal Nanoparticles in Microbiology, M. Rai & N. Duran (eds.) pp. 37-74. (Year: 2011).
Malhotra, Ankit; Kunzes Dolma, Navjot Kaur, Y.S. Rathore, Ashis, S. Mayilraj, Anirban Roy Choudhury. "Biosynthesis of gold and silver nanoparticles using a novel marine strain of Stenotrophomonas." Bioresource Technology. 142 pp. 727-731. (Year: 2013).
Kumar, Rakshak and Machmillan Nongkhlaw, Celin Acharaya, Santa Ram Joshi. "Bacterial Community Structure from the Perspective of the Uranium Ore Deposits of Domiasiat in India." Proc. Natl. Acad. Sci., India, Section B Biol. Sci. Thirteen pages. DOI: 10:1007/s40011-013-0164-z (Year: 2013).
He, Zhiguo and Shuzhen Li, Lisha Wang, Hui Zhong. "Characterization of Five Chromium-Removing Bacteria Isolated from Chromium-Contaminated Soil." Water Air Soil Pollut. 225: 1904. Ten pages. DOI: 10.107/s11270-014-1904-2 (Year: 2014).

* cited by examiner uncoated pins  silver-coated pins  gold-coated pins via dental technique  gold-coated pins via vacuum deposition a)

b)

a)

b)

BIOLOGICAL PROCESSING OF SCRAP METAL, HOUSEHOLD WASTE AND/OR INDUSTRIAL WASTE FOR THE ISOLATION OF HEAVY METALS

CROSS-REFERENCE TO RELATED APPLICATIONS

This application is the U.S. National Stage of International Application PCT/EP2016/056927, filed Mar. 30, 2016, which designates the U.S. and was published by the International Bureau in English on Oct. 6, 2016, and which claims the benefit of European Patent Application No. 15 161 646.3, filed Mar. 30, 2015; all of which are hereby incorporated herein in their entirety by reference.

PARTIES TO A JOINT RESEARCH AGREEMENT

The claimed invention was made under a joint research agreement between B.R.A.I.N. Biotechnology research and Information Network AG, Germany, and CyPlus GmbH, Germany. The joint research agreement was in effect before the effective filing date of the claimed invention, and the claimed invention was made as a result of activities undertaken within the scope of the joint research agreement.

FIELD OF THE INVENTION

The invention relates to an assay for identifying a bacterium capable of binding heavy metals such as gold and/or silver. The present invention also relates to a process of isolating or enriching a heavy metal such as gold and/or silver, e.g. from ore (such as mineral ore) or from scrap metal, household waste and/or industrial waste. The invention further relates to a use of a bacterium for isolating or enriching heavy metal such as silver and/or gold.

BACKGROUND OF THE INVENTION

Recent decades have seen a continued depletion of high-grade mineral resources and, concomitantly, a growing demand for precious metals. The demand for gold is unbowed. At the same time, the awareness for environmental problems associated with conventional mining techniques has grown significantly.

Gold (Au): Gold is one of the rarest elements on earth. In seawater, which constitutes the largest reservoir of gold, its concentration is only 0.01 mg/m$^3$, while on average 1-2 g/t is found in the upper crust of earth. In this environment, gold mostly occurs as pure metal) (Au$^0$, electrum (Ag/Au), gold-containing minerals and tiny inclusions are found in large volumes of material, usually rock. Furthermore, it is found (often in association with quartz) as telluride (AuTe$_2$) and selenide (AuSe$_2$) or locked in the lattice of minerals such as pyrite and arsenopyrite (invisible gold). Yields of gold obtained by commercial mining are currently between 0.5 and 13.7 g gold/t rock, with a tendency to increasingly exploit low-grade ores due to a shortage in higher grade ones.

Silver (Ag): Silver is about 20 times more abundant than gold. The majority of silver commercially accessible to date is deposited as metallic silver. But also sulphidic minerals (Ag$_2$S, acanthite) and AgCl (cerargyrit) often occur. Like gold, also silver minerals are often found embedded in silica matrices (quartz) in particle sizes in the range of nano- to micrometers.

A number of living microorganisms, but also nonviable, inactivated cells have the ability to bind metal ions. In the first case, metal binding can occur via adsorption to the cell surface or via active intracellular accumulation of metal ions. In the latter case of nonviable, inactivated cells—that is often referred to as biosorption—metal ion binding is believed to occur exclusively via surface adsorption. The biosorption capacity as a general characteristic of biomass results from the presence of chelating groups (e.g. carboxyl-, amide-, hydroxyl-, phosphate-, and thiol-groups) contributed by carbohydrates, lipids and proteins that are displayed on the cell surface. It has been described that amounts of metals of up to 50% of the cell dry weight can be accumulated by biomass (Vieira and Volesky (2000) "Biosorption: a solution to pollution?" Int Microbiol 3(1): 17-24). U.S. Pat. No. 5,055,402 discloses a process for removing metal ions from aqueous solution, using a matrix prepared from metal-binding microorganisms that have been immobilized and heat-inactivated at temperatures of 300-500° C. EP 0 432 935 B1 describes the adsorption of soluble metal-cyanide complexes also from aqueous solution by living biomass.

Traditionally, precious metals such as gold and/or silver have been recovered by placer (sediment) mining or hard rock mining using gravity and pyrometallurgical methods. Due to the exhaustion of metal-rich ores, hydrometallurgical techniques are increasingly employed to recover precious metals from low-grade sources. Methods for precious metal recovery, particularly gold, are work-intensive and require the use of heavy machines as well as of hazardous and recalcitrant chemicals. Nowadays, about 90% of the common industrial processes for the recovery of precious metals are based on cyanidation methods, since cyanide is one of the very few substances that are able to dissolve gold. In order to allow cyanide ions or other compounds to access a large portion of the metal enclosed in its ores, ores are generally ground to small particle sizes. However, the conventional method of separation of precious metals using cyanide leaching is problematic for the environment as well as for human health. Therefore, more environment-friendly processes would be desirable.

WO2009/130006 describes a procedure for isolating metals, notably precious metals, or their compounds from particulate material such as mineral ores using certain biomass. The biomass binds the metal or the metal compound by cell components of the organisms. After separation of the biomass from unbound material of the particulate material, the metal or a compound of said metal can be isolated from the biomass. However, identifying biomass or other material suitable for such process is not an easy task.

Departing from the prior art, it is an object of the invention to provide a methodology for identifying material capable of binding a heavy metal such as gold and/or silver. It is another object of the invention to provide a process of isolating a heavy metal such as gold and/or silver from material containing the heavy metal such as gold and/or silver.

SUMMARY OF THE INVENTION

Accordingly, the present invention provides inter alia:
1. A process of isolating or enriching a heavy metal such as gold and/or silver present in a liquid medium, comprising
    a step of incubating a liquid medium containing a heavy metal and biomass comprising a bacterium capable of binding the heavy metal;
    a step of separating the biomass having bound heavy metal from the liquid medium of the previous step; and a step of isolating the heavy metal from the biomass separated in the previous step.
2. The process according to item 1, wherein said bacterium belongs to the genera *Pseudochrobactrum* or *Stenotrophomonas*.
3. The process according to item 1 or 2, wherein said bacterium is selected from the following species: *Pseudochrobactrum asaccharolyticum*, *Bacillus subtilis*, *Bacillus pumilus*, *Pseudomonas fluorescens*, *Stenotrophomonas maltophilia*, *Bacillus cereus*, and *Pseudomonas aeruginosa*.
4. The process according to any one of items 1 to 3, wherein said bacterium is selected from:
*Pseudochrobactrum asaccharolyticum* (DSM-25619), *Bacillus subtilis* subsp. subtilis (DSM-10), *Bacillus pumilus* DSM-27, *Pseudomonas fluorescens* (DSM-50090), *Stenotrophomonas maltophilia* (DSM-50170), *Bacillus cereus* (DSM-31), and *Pseudomonas aeruginosa* (DSM-50071).
5. The process according to any one of items 1 to 4, wherein said biomass comprises living biomass and/or dead biomass.
6. The process according to any one of items 1 to 5, wherein the incubating step comprises agitating the liquid medium containing the heavy metal and the biomass for forming, film or foam containing biomass having bound heavy metal; and the separating step comprises removing the film or foam from the liquid medium.
7. The process according to any one of items 1 to 6, wherein the incubation step is conducted in a reactor comprising an agitator for agitating the liquid medium.
8. The process according to any one of items 1 to 7, wherein said heavy metal is selected from ruthenium, rhodium, palladium, silver, osmium, iridium, platinum, gold, and/or rare earth metals, preferably the heavy metal is silver and/or gold.
9. The process according to any one of items 1 to 8, wherein said heavy metal present in said liquid medium is in elemental form or is a compound of said heavy metal.
10. The process according to any one of items 1 to 9, wherein said liquid medium is a suspension containing particulate material containing the heavy metal.
11. The process according to item 10, wherein said particulate material contains the heavy metal in an amount of at most 10000 ppm by weight, preferably at most 1000 ppm by weight, more preferably at most 100 ppm by weight, even more preferably at most 10 ppm by weight, even more preferably at most 1 ppm by weight, and even more preferably at most 0.1 ppm by weight.
12. The process according to item 10 or 11, wherein said particulate material is a mineral ore such as a sulfidic or oxidic mineral ore, scrap metal, household and/or industrial waste.
13. The process according to any one of items 10 to 12, wherein said particulate material has a particle size of at most 400 µm, preferably at most 300 µm, more preferably at most 200 µm or even more preferably at most 100 µm determined by sieving.
14. The process according to any one of items 1 to 13, wherein the incubating step is preceded by or comprises a step of biooxidation said mineral ore as said particulate material for releasing from said mineral ore silver or gold or for increasing accessibility of the biomass to silver or gold in the mineral ore.
15. The process according to any one of items 10 to 13, wherein said suspension contains, in the separating step, a cell dry weight of said biomass in an amount of from 0.01 to 20% (w/w), preferably in an amount of from 0.05 to 0.5% (w/w), based on the weight of the ore contained in the suspension.
16. The process according to any one of items 10 to 13, wherein said suspension contains a cell dry weight of said biomass in an amount of from 0.01 to 20% (w/w), preferably in an amount of from 0.05 to 0.5% (w/w), based on the weight of the scrap metal, household and/or industrial waste contained in the suspension.
17. A process of isolating or enriching a heavy metal present in a liquid medium (e.g. a suspension), comprising
a step of incubating a suspension containing (i) a particulate ore containing a heavy metal in elemental form and (ii) biomass comprising a bacterium, or a combination of two or more bacteria, capable of binding the heavy metal;
a step of separating the biomass having bound heavy metal from the suspension of the previous step; and
a step of isolating the heavy metal from the biomass separated in the previous step,
optionally as further in any one or more of the items above or features given below.
18. The process according to item 17, wherein said suspension contains the ore, in the separating step, in an amount of from 1 to 50% (w/w), preferably from 10 to 25% (w/w) based on the total weight of the suspension.
19. A process of isolating or enriching a heavy metal present in a liquid medium (e.g. a suspension), comprising
a step of incubating a suspension containing (i) scrap metal, household waste and/or industrial waste containing a heavy metal in elemental form and (ii) biomass comprising a bacterium, or a combination of two or more bacteria, capable of binding the heavy metal;
a step of separating the biomass having bound heavy metal from the suspension of the previous step; and
a step of isolating the heavy metal from the biomass separated in the previous step,
optionally as further in any one or more of the items above or features given below.
20. Use of a bacterium selected from the genera *Pseudochrobactrum* and *Stenotrophomonas*, or selected from the group of species consisting of *Pseudochrobactrum asaccharolyticum*, *Bacillus subtilis*, *Bacillus pumilus*, *Pseudomonas fluorescens*, *Stenotrophomonas maltophilia*, *Bacillus cereus*, and *Pseudomonas aeruginosa*, for isolating or enriching a heavy metal, preferably elemental gold and/or silver.
21. An assay for identifying a bacterium capable of binding elemental heavy metal such as gold and/or silver, comprising the following steps:
cultivating a test bacterium in a suitable first culture medium;
immersing at least a surface portion of a test tool into the first culture medium for a second predetermined period of time, said surface portion being coated by elemental heavy metal, respectively;
removing said test tool from said first culture medium and optionally rinsing the test tool;
contacting a second culture medium with the surface portion coated by elemental heavy metal of said test tool removed in the previous step; and
identifying the test bacterium as being capable of binding elemental heavy metal from growth of the test bacterium in said second culture medium.
22. The assay of item 21, wherein said container is part of a multi-well plate and said test tool is a pin on the cover lid of the multi-well plate, said pin being coated by elemental heavy metal, preferably elemental silver or gold, at least on a tip portion of the pin, wherein said pin extends downwards from the cover lid into said container such that the tip of the pin is immersed into the first culture medium in step (ii).

23. The assay of item 21 or 22, wherein said second culture medium that may be an agar plate contains a, preferably soluble, salt of the heavy metal, preferably an optionally soluble, salt of gold and/or silver, respectively, for selecting test bacteria capable of growing in the presence of said salt of the heavy metal, preferably the salt of the gold and/or silver.

The inventors have found a method for identifying bacteria capable of binding a heavy metal such as gold and/or silver, preferably in non-ionic form. The method can be performed on multi-well format and therefore allows screening of many bacterial strains in parallel. The method allows combining two selection criteria, namely binding of bacteria to heavy metal such as gold and/or silver coated surfaces and selection in media containing a compound of the metal. Accordingly, bacterial strains capable of binding heavy metal such as gold and/or silver can be identified with high efficiency. Biomass of bacteria identified by the assay of the invention or by other means can be used for isolating the heavy metal such as the gold and/or silver from liquid medium, preferably a suspension, containing the heavy metal such as the gold and/or silver, respectively.

DETAILED DESCRIPTION OF THE INVENTION

Figure 1:
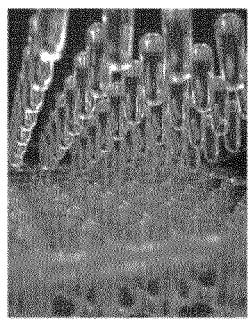
FIG. 1: Lids for 96 well microplates with pins. From left to right: uncoated, silver coated, gold coated via dental techniques, gold coated via vacuum deposition.
Figure 1:
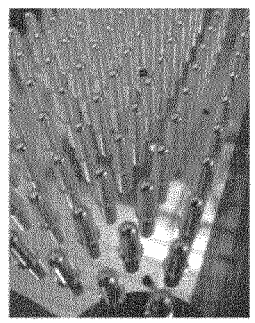
Figure 1:
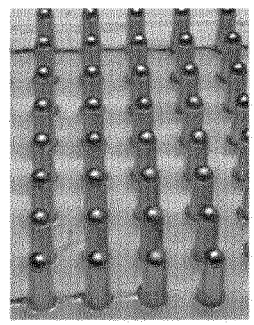
Figure 1:
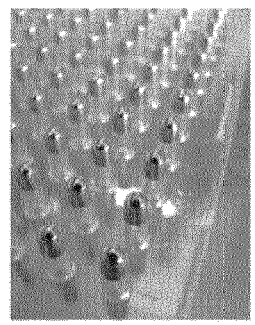

In the assay for identifying a bacterium capable of binding elemental heavy metal such as gold and/or silver, a test bacterium is first cultivated in a culture medium suitable for the test bacterium. The assay may also be used for identifying microorganisms other than bacteria, such as archaea or fungi. The cultivating step may be performed in a suitable container, the type of which is not particularly limited and any container known for cultivation of bacteria can be used including containers made from glass or plastic. The size of the container is also not limited. However, it is preferred to conduct the assay with small volumes of culture medium of from 0.2 to 100 ml, preferably from 0.3 to 20 ml, more preferably from 0.5 to 10 ml, and even more preferably from 1 to 3 ml. The container may be a well of a culture plate. In one embodiment, the assay is performed with many test bacteria in parallel and/or with the same bacteria in parallel under different conditions or in different culture media. For such purpose, multi-well plates may be used.

The culture medium or culture media to be used depend(s) on the type of bacteria to be cultivated. Suitable culture media are known for many bacteria and other microorganisms. A medium suitable for culturing many bacteria is Luria-Bertani medium. The time for cultivation may be selected such that the bacteria are in a growth phase suitable for binding heavy metal such as gold and/or silver. A growth state suitable for binding of heavy metal such as gold and/or silver may be an exponential growth phase. However, other growth phases such as a stationary phase may also be tested. Thus, the method is also usable as an assay for identifying suitable conditions for binding elemental heavy metal such as gold and/or silver by a bacterium or other microorganism. Conditions to be tested may be growth phase, culture medium, temperature, buffer, pH, cell density etc.

In step (i), the test bacterium is cultivated for achieving a suitable cell density of the test bacteria for the subsequent step. The cultivation time may be very short such as some minutes if the test bacterium was inserted into the container already at a cell density suitable for the subsequent steps. Alternatively, the cultivation time may be several hours if the test bacterium was inoculated in a small concentration into the first culture medium present in the container.

In step (ii) of the assay, at least a surface portion of a test tool is contacted with the test bacterium in the culture medium. The test tool has a surface portion that is coated with elemental heavy metal such as elemental gold and/or elemental silver, or has a coating containing elemental heavy metal such as gold or silver. A test bacterium having the capability of binding elemental heavy metal such as elemental gold and/or elemental silver will bind to the gold and/or silver containing coating on said surface portion of the test tool. There are several methods of coating the surface portion or the entire test tool with elemental heavy metal such as gold and/or silver. One method is electrodeposition of elemental heavy metal such as gold and/or silver from heavy metal (e.g. gold and/or silver) compounds in an aqueous solution (electroplating), which is a method generally known in the art of surface treatment. Another method applicable is chemical vapor deposition (CVD).

The test tool may be of elongated shape having the coated surface portion at one end thereof. This allows easy immersion of at least the coated surface portion into the first culture medium. The test tool may be connected to a lid of the container at an end of the test tool opposite to the end where the coated surface portion is located. In this way, the test tool can be immersed into the culture medium when the lid covers a part of or the entire top opening of the container. In step (ii), a lid of the container present during the cultivation of step (i) may be removed from the container and replaced by the lid-test tool assembly, whereby the coated surface portion is immersed into the first culture medium. Alternatively, the entire cultivating step (i) may be conducted with the test tool immersed into the culture medium, e.g. by covering the container with the assembly comprising a lid and the test tool during step (i). In the latter case, the lid may not cover the top opening of the container completely for allowing exchange of air with the culture medium in the container. In embodiments where multiple assays are conducted in parallel such as on culture plates, the lids of all wells may bear a test tool for immersion into the culture media of the wells. In such case, the test tool may be a pin on each cover lid of a multi-well plate, whereby the pins are coated by elemental silver or gold at least on a tip portion of the pin. The pins may extend downwards from the cover lid into the container or well such that the tip of the pin is immersed into the first culture medium.

For reproducibility, the test tool should be immersed, with its coated surface portion, into the first culture medium for a predetermined period of time. This period of time should be sufficient for allowing specific adherence of test bacteria that can bind elemental heavy metal such as gold and/or silver. The predetermined period of time may be at least 10 second, but is preferably at least 1 minute, more preferably at least 30 minutes. The upper limit of the period of time is not particularly limited, but beyond 48 hours, no further or more specific adherence of test bacteria to the coated surface portion is expected.

When the predetermined period of time is over or at any other time deemed suitable by the user, the test tool is removed from the culture medium. Preferably, the coated surface or the entire test tool is rinsed or washed for removing not-specifically bound or weakly bound test bacteria from the test tool. For rinsing, a rinsing solution may be used that may be a sterile aqueous buffer or sterile culture medium compatible with the test bacteria.

The test tool or at least the coated surface portion thereof is then contacted with a second culture medium for inoculating the second culture medium with any test bacteria adhering to the surface portion of the test tool. The second culture medium should be sterile before contacting it with the test tool. The second culture medium may be the same culture medium or a different culture medium to that used in step (i). In one embodiment, the second culture medium is a solid or semi-solid culture medium such as an agar plate. If a multi-well plate is used in step (i), a multi-well plate of the same size, shape and arrangement of wells may be used in this step for allowing automation of the entire assay.

The second culture medium may contain a, preferably water soluble, compound of the heavy metal such as gold and/or silver for selecting test bacteria capable of growing in the presence of said soluble compound of the heavy metal such as gold and/or silver, respectively. Generally, the compound of the heavy metal in the second culture medium is or contains a compound of the same metal that is coated on the test tool. This allows a second selection step for identifying a bacterium capable of binding elemental heavy metal such as gold and/or silver. It is, however, also possible to employ, additionally or alternatively, a compound of a heavy metal in the second culture medium different from the metal that is coated on the test tool. The compound of the heavy metal such as gold and/or silver may be a, preferably water soluble, salt of a heavy metal such as gold and/or silver. The concentration of the compound or salt of the heavy metal such as gold and/or silver in said culture medium may be suitably determined as described in the Examples. An example of soluble gold compound is $HAuCl_4$. An example of a soluble silver compound is $AgNO_3$. The soluble gold compound may be used in a concentration of from 50 µM to 1 mM, preferably of from 100 to 700 µM, more preferably of from 250 to 600 µM. The soluble silver compound may be used in a concentration of from 20 µM to 1 mM, preferably of from 50 to 600 µM, more preferably of from 150 to 500 µM.

A test bacterium being capable of binding elemental heavy metal such as gold and/or silver may be identified from growth of the test bacterium in said second culture medium. The second culture medium may be inspected or analyzed for bacterial growth after a predetermined cultivation time which may be after between 5 and 48 hours, preferably after 10 to 20 hours. This identification may be supported using commercially available plate readers or using photography of the second culture medium.

Bacterial strains capable of binding elemental gold and/or silver and identifiable by the assay described above are selected from the following genera and species: *Pseudochrobactrum*, preferably *Pseudochrobactrum asaccharolyticum*, *Bacillus subtilis*, *Bacillus pumilus*, *Pseudomonas fluorescens*, *Stenotrophomonas*, preferably *Stenotrophomonas maltophilia*, *Bacillus cereus*, and *Pseudomonas aeruginosa*. Specific examples of such bacterial strains are: *Pseudochrobactrum asaccharolyticum* (DSM-25619), *Bacillus subtilis* subsp. *Subtilis* (DSM-10), *Bacillus pumilus* DSM-27, *Pseudomonas fluorescens* (DSM-50090), *Stenotrophomonas maltophilia* (DSM-50170), *Bacillus cereus* (DSM-31), and *Pseudomonas aeruginosa* (DSM-50071). The "DSM" numbers refer to deposit numbers of the Deutsche Sammlung von Mikroorganismen and Zellkulturen GmbH. In another embodiment, the bacterium is selected from *Pseudochrobactrum*, preferably *Pseudochrobactrum asaccharolyticum*, *Pseudomonas fluorescens*, *Stenotrophomonas*, preferably *Stenotrophomonas maltophilia*, and *Pseudomonas aeruginosa*.

Bacterial strains identified or identifiable by the assay of the invention, notably those listed above, may be used as biomass in a process of isolating or enriching heavy metal such as gold and/or silver. The biomass may contain bacteria selected from the genera, species or strains listed above. The biomass may comprise a combination of two or more bacteria, such as two or more bacterial strains or bacterial genera. The biomass may comprise a combination of three or more bacteria, such as three or more bacterial strains or bacterial genera.

The process of isolating or enriching heavy metal such as gold and/or silver is generally performed in a liquid medium. The biomass binds the heavy metal such as gold and/or silver by cell components of the bacteria. After separation of the biomass from unbound material, the heavy metal such as gold and/or silver can be isolated from the biomass. The invention allows isolating heavy metal such as gold and/or silver from material that contains only low amounts of heavy metal such as gold and/or silver without the use of hazardous cyanide leaching and/or amalgam processing. The material from which the heavy metal is isolated and/or enriched may contain the heavy metal in an amount of at most 10000 ppm by weight, preferably at most 1000 ppm by weight, more preferably at most 100 ppm by weight, even more preferably at most 10 ppm by weight, even more preferably at most 1 ppm by weight, and even more preferably at most 0.1 ppm by weight. The process of the invention provides an environmentally innocuous access to heavy metal such as gold and/or silver that requires little energy and avoids pollution of the environment.

The biomass according to the invention can comprise living biomass, i.e. the biomass can contain living bacteria. However, it was surprisingly found that dead biomass can also be used, in particular biomass that contains dead bacteria. Thus, in a preferred embodiment of the invention, a biomass is used which comprises at least 70% dead biomass, in particular at least 70% dead bacterial cells, preferably at least 80 or 90% dead biomass, in particular at least 80 or 90% dead bacterial cells, more preferably at least 95 or at least 99% dead biomass, in particular at least 95 or at least 99% dead bacterial cells. In one embodiment, biomass is used which comprises at least 99.9% dead biomass, in particular at least 99.9% dead bacterial cells.

In case of living biomass, dead bacterial cells may additionally be present. If living biomass or bacteria are used, the liquid medium used in the process of isolating or enriching heavy metal such as gold and/or silver preferably contains suitable nutrients for enabling growth and survival of the bacteria in the liquid medium. The latter may not be necessary if dead biomass is used. Dead biomass may be obtained from living biomass of the bacteria selected from the genera, species or strains listed above. Dead biomass is characterized by the inability to proliferate and/or to maintain metabolic functions. Dead biomass may contain less than 10% living bacterial cells, preferably less than 5% living bacterial cells, more preferably less than 1%, even more preferred less than 0.01% living bacterial cells in terms of number of cells based on the total number of cells in a sample of the biomass. The dead biomass may be obtained by culturing living biomass containing bacteria in aqueous media until suitably high cell densities are obtained. The bacterial cells may be separated from the liquid medium, e.g. by sedimentation, notably by centrifugation, or other means such as filtration to obtain a wet biomass. The separated wet biomass may then be inactivated for obtaining dead biomass. Inactivation can be achieved for example by applying heat and/or high pressure to the biomass, in processes known in the art such as pasteurization or autoclaving. The wet biomass may be dried by reducing the content of solvent. Drying may be done at elevated temperature and/or under vacuum. The drying step generally kills most of the bacterial cells, whereby dead biomass of the bacteria is obtained. In a preferred method for obtaining dead biomass, living bacterial cells or the wet biomass may be sterilized at elevated temperature, optionally with additional application of pressure. Sterilization may be performed at a temperature of from 60° C. to 140° C., preferably at from 70° C. to 130° C., more preferably at from 80° C. to 121° C. The duration of sterilization may be adjusted to the temperature applied, whereby longer durations are used where the temperature is on the lower side of the ranges mentioned before. Generally, sterilization may be done for 5 min to 3 hours, preferably from 10 minutes to 60 minutes. In one embodiment, the temperature is from 60° C. to 90° C. and the duration is from 1 hour to 3 hours. In another embodiment, the temperature is from 90° C. to 130° C. and the duration is from 10 minutes to 30 minutes. The optional additional application of pressure may be from 0.5 to 5 bar, preferably from 1 to 3 bar (above ambient pressure). Specific examples for conditions usable for sterilization or inactivation of the bacterial cells are 121° C. for 20 minutes, 1 bar, and 80° C. for 1 h. The dead biomass may be stored until use in the process of the invention.

For carrying out the process of isolating or enriching heavy metal such as gold and/or silver, dead or living biomass of a bacterium that is known to be able to specifically adsorb heavy metal such as gold and/or silver is incubated, preferably agitated, in a liquid medium containing heavy metal such as gold and/or silver. The heavy metal such as gold and/or silver contained in the liquid medium may derive from any material containing heavy metal such as gold and/or silver such as elemental heavy metal (such as elemental gold and/or silver) or compounds of heavy metal (such as compounds of gold and/or silver), mineral ore, scrap metal or other waste material (e.g. household or industrial waste). In one embodiment, the heavy metal such as gold and/or silver to be isolated or enriched is present in solid material from which the heavy metal such as gold and/or silver can be isolated or enriched. Solid material, such as mineral ore, scrap metal, solid household or solid industrial waste, containing heavy metal such as gold and/or silver is preferably crushed, milled or pulverized for obtaining particulate material before inserting it into the liquid medium, and may be pre-treated using methods suitable to facilitate metal release, such as biooxidation or incubation with microorganisms that produce corrosive metabolites. The liquid medium may be a suspension of solid material forming a solid phase in the liquid phase of the liquid medium.

The incubating step of the process may take place in a continuous-flow, stirred-tank reactor or open pond such as used in waste-water treatment plants. In this environment, parameters that are important for microbial growth (pH, temperature, nutrients) can be controlled and therefore, bacteria can be stably maintained over space and time. Generally, the liquid medium is agitated during the incubation step, followed by a separation step. In one embodiment, a flotation procedure can be applied in which the liquid medium is agitated such that a film or foam containing the biomass having bound heavy metal such as gold and/or silver is formed on the top of the liquid medium. The film or foam may be removed from the top of the liquid medium, and heavy metal such as gold and/or silver can be isolated from the film or foam. In another embodiment, a density gradient may be applied to the liquid medium to separate the biomass in a layer of the liquid medium, and the layer containing the biomass may be separated from the liquid medium e.g. by aspiration. In another embodiment, the biomass may be sedimented in the liquid medium and the layer containing the sedimented biomass may be separated from the liquid medium by removing the supernatant.

In the process of the invention, a huge concentration effect can generally be achieved by binding a heavy metal such as gold and/or silver from low grade material to the biomass. Thus, the biomass separated from the liquid medium and having bound heavy metal typically has a mass that is significantly lower than the mass of the heavy metal containing material used at the outset. This concentration effect allows transporting the biomass separated from the liquid medium, optionally in a dried state, over long distances, where transport of an amount of the original heavy metal containing material would not be economical. Thus, the invention allows separation of the location where the incubating and separating steps are performed from the location where the isolating step is performed.

In the present invention, heavy metal may be heavy metal in free, elemental form (non-ionic or mineral) or a compound such as a salt or salts of the heavy metal. The heavy metal may be selected from ruthenium, rhodium, palladium, silver, osmium, iridium, platinum, gold, and rare earth elements (REE). The REE may be selected from lanthanum, cer, praseodym, neodym, promethium, samarium, europium scandium, yttrium, gadolinium, terbium, dysprosium, holmium, erbium, thulium, ytterbium, and lutetium. In a preferred embodiment, the heavy metal is silver and/or gold.

A metal in elemental form has bonds between metal atoms and oxidation state 0. If the heavy metal such as the gold and/or silver isolated or enriched in the invention is in elemental form, it may form nanoscale particles such as metal clusters. Nanoscale particles of the heavy metal such as the gold and/or silver and clusters thereof may have ligands that occupy free valencies of metal atoms located on the surface of the nanoscale metal particles or clusters. Clusters of elemental heavy metal such as the gold and/or silver may comprise from 2 to 1000 metal atoms. In another embodiment, the clusters may comprise from 3 to 500 metal atoms. In further embodiments, the clusters may comprise from 5 to 400 or from 20 to 300 metal atoms. In general, nanoscale particles have a size of <500 nm, in another embodiment of <100 nm, in a further embodiment of <50 nm, and in a still further embodiment of <10 nm. A metal in elemental form is typically insoluble in aqueous media. However, nanoscale elemental heavy metal such as such as gold and/or silver metal or clusters thereof may be dispersed or dispersible in aqueous media, e.g. in the form of a colloid.

In compounds of the heavy metal such as the gold and/or silver gold and/or silver, the metal atoms may have an oxidation state of 0 or may be oxidized. It is also possible that a metal compound contains metal atoms in 2 or more different oxidation states. The heavy metal such as the gold and/or silver compound may be a salt of the heavy metal such as the gold and/or silver. A compound of heavy metal such as the gold and/or silver may be soluble or insoluble in aqueous solution. In one embodiment, the compound of the heavy metal such as the gold and/or silver is essentially insoluble in water at pH 7.0 and 25° C. Essentially insoluble means that 1 l of pure water dissolves at most 10 mg of said compound at pH 7.0 at 25° C. If it is insoluble or essentially insoluble in water at pH 7.0 at 25° C., the compound of heavy metal such as the gold and/or silver present in a material such as a mineral ore may be finely dispersed or dispersible in water e.g. in the form of a colloid.

In the process of the invention, the heavy metal such as the gold and/or silver may undergo a chemical reaction e.g. when bound to or separated from said biomass. Thus, the metal isolated in the isolating step may be in a chemical form different from the chemical form at the outset of the process of the invention. The present invention covers processes wherein the chemical state of a metal to be isolated changes in the course of the process. It is possible that the heavy metal such as the gold and/or silver to be isolated contains the metal in two or more different chemical states or compounds.

The material containing heavy metal such as the gold and/or silver to be isolated may be any material such as a mineral ore. The material may also by scrap metal, household waste and/or industrial waste. The material is generally particulate material. The material may contain high amounts of silicates or quartz. The mineral ore may be a mining waste material obtained in a process of isolating a desired component other than the metal of the invention from a mineral ore. The material may for example be or contain a sulfidic mineral material such as pyrite. In one embodiment, the heavy metal such as the gold and/or silver, notably the elemental gold and/or silver, of the invention is finely distributed in the material such as an elemental metal locked in the crystal lattice of a mineral such as pyrite. Such extremely fine distributed or dispersed elemental metal is generally referred to as "invisible metal"; if the metal is gold, it is referred to as "invisible gold".

In the incubating step of the process of the invention, an aqueous mixture is prepared using material containing heavy metal such as gold and/or silver and the biomass of the invention. The particulate material such as the particulate mineral ore to be used should be finely ground. For this purpose, the incubating step may be preceded by a grinding step. The particulate material may have a particle size, determined by sieving, of at most 5 mm. Alternatively, the particulate material may have a particle size of at most 1 mm, of at most 400 µm, or of at most 100 µm determined by sieving. In a further embodiment, the particles are smaller than 100 µm smaller than 50 µm or smaller than 10 µm, which may be achieved by sieving of a ground material. The yield of the process of the invention is the higher, the smaller the particle size of the particulate material used in the incubating step.

The incubating step is typically conducted in reactors, e.g. as are used in waste-water treatment. The reactor preferably contains an agitation system for agitating the aqueous mixture. The reactor may be a stirred-tank reactor and can be operated in a batch or continuous-flow mode. The reactor may be equipped with devices for measuring and controlling parameters such as temperature, pH, nutrient content etc. Such means are known in the art. The liquid medium or mixture prepared for the incubating step generally is an aqueous medium or mixture. The liquid medium or mixture contains the biomass as well as the heavy metal such as gold and/or silver to be isolated or enriched. The liquid medium can be used for controlling conditions for binding the heavy metal such as gold and/or silver by the biomass, such as temperature, concentration of biomass and material containing the heavy metal such as gold and/or silver, pH, ionic strength etc. The liquid medium or mixture may further include media with nutrients required for the growth of the biomass, where the biomass used is or contains living bacterial cells to be used for isolating or enriching the heavy metal such as gold and/or silver. Suitable growth conditions and nutrient requirements for the biomass used can be obtained from the general prior art on microbiology. Suitable growth conditions are also provided by collections of microorganisms such as the American Type Culture Collection (ATCC) or the German Collection of Microorganisms and Cell Cultures (Deutsche Sammlung von Mikroorganismen and Zeilkulturen GmbH, DSMZ) where suitable bacterial strains can be obtained from. Further, the aqueous medium or mixture contains the biomass used for binding the gold and/or silver to be isolated. Typically, the biomass is added to the reactor at such an amount that the concentration in the reactor allows for further growth of the biomass. For this purpose, one or more pre-cultures may be grown in separate reactors for maintaining sufficiently large amounts of the biomass in aqueous suspension to be used. Alternatively, dead biomass is used for isolating or enriching the heavy metal such as gold and/or silver as described above. In this case, the dead biomass is added to the liquid medium or mixture.

The amount or concentration of biomass in the liquid medium or mixture is not particularly limited. However, if too little biomass is present, not all heavy metal such as gold and/or silver that is accessible for binding may be bound by the biomass. If more biomass is used than is needed for binding the available heavy metal such as gold and/or silver, this may not be economical and, at some point, agitation may become difficult due to high viscosity caused by the biomass. A suitable amount of biomass to be used on the large-scale may be determined by a number of smaller scale experiments, wherein the amount or concentration of biomass for a given heavy metal such as gold and/or silver-containing material is determining by measuring the amount of the heavy metal such as gold and/or silver, respectively, that can be bound by the biomass or that remains in the material that originally contained the heavy metal such as gold and/or silver.

The content of particulate material (such as mineral ore) in the aqueous medium or mixture of the incubating step may, for example, be between 1 kg and 500 kg particulate material per m³ of the aqueous mixture. Alternatively, said content may be between 5 kg and 100 kg particulate material per m³ of the aqueous mixture. Similarly, as described above with regard to the amount or concentration of biomass to be used, a suitable amount of particulate material may be determined experimentally in small scale experiments before carrying out larger scale processes.

In the incubating step of the process of the invention, the aqueous medium is incubated for allowing binding of the heavy metal such as gold and/or silver by the biomass. The incubation time depends on the rate of binding. Generally, the incubation time is between 0.5 hours and 96 hours, preferably between 0.5 hours and 48 hours, more preferably between 1 and 48 hours, more preferably between 1 hour and 24 hours and most preferably between 3 and 24 hours. The temperature of incubation depends mostly on the type of biomass used. Temperature control may be used for controlling growth of said biomass. During incubation, parameters in the liquid medium or mixture such as pH, nutrient content, temperature etc. are monitored and, if necessary, controlled for maintaining desired incubation conditions.

In the incubating step, the liquid medium is preferably agitated using an agitator and is intimately mixed for forming a film or foam containing biomass on the top of the medium. It is, however, not necessary that agitation is performed during the entire incubation time. Optionally, a gas such as air is introduced into the reactor for supporting formation of a film or foam on the surface of the liquid medium.

After the incubating step, the separating step may be conducted. After the incubating step, remaining particulate material may be allowed to settle and may be removed. If a film or foam containing biomass having bound heavy metal such as gold and/or silver was produced, the film or foam may then be removed from the top of said liquid medium. Alternatively, the biomass having bound heavy metal is separated by other methods such as sedimentation. The separated biomass may, depending on the subsequent step, be dried for facilitating storage and/or transport of the biomass before the isolating step is performed. The liquid medium (such as the suspension) may contain, in the separating step, a cell dry weight of the biomass in an amount of from 0.01 to 20% (w/w) based on the weight of the ore or based on the particulate scrap metal, household waste and/or industrial waste contained in the liquid medium (or the suspension). Preferably, the liquid medium (or suspension) contains a cell dry weight of said biomass in an amount of from 0.05 to 5% (w/w), preferably from 0.05 to 0.5% (w/w), based on the weight of the ore or based on the weight of the particulate scrap metal, household waste and/or industrial waste contained in the liquid medium or suspension.

If the particulate material is a mineral ore, the liquid medium may contain, in the separating step, the ore in an amount of from 1 to 50% (w/w), preferably from 10 to 25% (w/w) based on the total weight of the liquid medium. If the particulate material is a scrap metal, household waste and/or industrial waste, the liquid medium may contain, in the separating step, the scrap metal, household waste and/or industrial waste in an amount of from 1 to 50% (w/w), preferably from 10 to 25% (w/w) based on the total weight of the liquid medium.

In the isolating step, termed biological separation process (BSP), heavy metal such as gold and/or silver bound to the biomass is isolated from said biomass. The heavy metal such as gold and/or silver may for example be desorbed from the biomass in a liquid phase using acidic or basic conditions. Alternatively, the biomass may be combusted to destroy and remove organic matter of said biomass. The metal may be purified from the residue and/or ashes of the biomass.

The process of the invention may be combined with process steps used for isolating metals from metal ores known from prior the art. In order to facilitate access of the biomass used in the invention to particles or compounds of heavy metals present in the particulate material, a known biooxidation step may be used in combination with the invention. For instance, if said particulate material is a sulfidic ore such as pyrite, sulfide-oxidizing bacteria such as Acidithiobacilli may be used for at least partially degrading the sulfidic mineral. Such biooxidation or bioleaching is described by (Rawlings and Johnson (2007) "The microbiology of biomining: development and optimization of mineral-oxidizing microbial consortia." Microbiology 153: 315-324). This treatment may be carried out before the incubating step of the invention or concurrently with this step by adding the biooxidation organism to the aqueous solution of step (i). Examples of biooxidation or bioleaching organisms are *A. ferrooxidans, A. thiooxidans, Leptospirillum ferrooxidans, T. organoparus, Thermothrix thiopara, Sulfolobus acidocaldarius,* and *S. brierleyi*. The process described in US 2007/107550 may also be used for the pre-treatment of recalcitrant ores, whereby the hydrometallurgical treatment step is replaced by the process of the present invention.

EXAMPLES

Example 1

Resistance-Assay

The growth of several microorganisms (e.g. *Escherichia coli, Xanthomonas campestris, Cupriavidus metallidurans* and *Bacillus sphaericus*) was monitored in the presence of the lids with coated pins. *Escherichia coli* and *Xanthomonas campestris* served as negative controls with regard to metal binding; *Cupriavidus metallidurans* as positive control. Additionally, *Bacillus sphaericus* was used as a positive control for silver binding. For *Bacillus sphaericus* the binding to gold particles and gold coated surfaces was observed earlier by the inventors. *Cupriavidus metallidurans* is a gram-negative, rod-shaped bacterium which has gold binding capacity as described in the literature (Reith et al., 2006). The species name *metallidurans* indicates its resistance to heavy metals and its ability to survive in the presence of gold and silver was investigated previously (Reith F, Rogers S L, McPhail D C and Webb D. (2006) " Biomineralization of gold: biofilms on bacterioform gold." *Science* 313(5784): 233-236; Reith F, Etschmann B, Grosse C, Moors H, Benotmane M A, Monsieurs P, Grass G, Doonan C, Vogt S, Lai B, Martinez-Criado G, George G N, Nies D H, Mergeay M, Pring A, Southam G and Brugger J. (2009) "Mechanisms of gold biomineralization in the bacterium Cupriavidus metallidurans." *Proc Natl Acad Sci* 106(42):17757-17762; Ledrich ML1, Stemmler S, Laval-Gilly P, Foucaud L, and Falla J (2005) "Precipitation of silver-thiosulfate complex and immobilization of silver by Cupriavidus metallidurans CH34." *Biometals* 18(6): 643-650).

To investigate the tolerated concentration of silver and gold, the microorganisms were propagated in liquid medium and streaked on agar plates with different concentrations of $AgNO_3$ or $HAuCl_4$, respectively. The results are shown in Table 1 and 2.

For establishing the screening resistance assay, the microorganisms were cultured, transferred into microplates and incubated for three hours at 28° C. with metal coated or uncoated pins, respectively. After incubation, the lids were washed in saline and subsequently stamped on metal-containing agar plates (Luria-Bertani medium), cultured over night at 28° C., so that the microorganisms went through a first and a second selection step. For selection on agar plates, the medium was finally supplemented with 200 μM AgNO$_3$ or 400 μM HAuCl$_4$, respectively.

Example 2

Binding Assay

An assay-system for detection of microbial gold- and silver binding capacity was developed in 96-well microplates to enable large-scale screening. For this assay 96-well MicroWell™ polystyrol plates and Nunc-Immuno™ TSP (Transferable Solid Phase) polystyrol lids were used. The lids were equipped with 96 pins reaching into the wells of the microplate to enable adhesion of the microorganisms. The lids with pins are available with different surface materials such as MaxiSorp™ (high affinity to molecules with hydrophilic and hydrophobic areas) or PolySorp™ (high affinity to hydrophobic molecules). The lids were either silver-coated or gold-coated via galvanic treatments with dental technical methods or gold coating was directly done via vacuum deposition (FIG. 1). The MaxiSorp™ surface was found to be most suitable for silver and gold coating and that the gold coating was mechanically stable, i.e. no erosion or disruption was observed after repeated use in 96-well plates comprising culture medium.

TABLE 1

Microbial growth in dependence on AgNO$_3$ concentration;
x = growth, (x) = weak growth

| AgNO$_3$ concentration | Cupriavidus metallidurans | Bacillus sphaericus | Xanthomonas campestris | Escherichia coli |
|---|---|---|---|---|
| 2 μM | x | x | x | x |
| 10 μM | x | x | x | x |
| 20 μM | x | x | x | x |
| 50 μM | x | x | x | x |
| 100 μM | x | x | x | x |
| 150 μM | x | x | | |
| 200 μM | (x) | | | |
| 400 μM | | | | |
| 1000 μM | | | | |

TABLE 2

Microbial growth in dependence on HAuCl$_4$ concentration;
x = growth, (x) = weak growth

| HAuCl$_4$ concentration | Cupriavidus metallidurans | Bacillus sphaericus | Xanthomonas campestris | Escherichia coli |
|---|---|---|---|---|
| 2 μM | x | x | x | x |
| 20 μM | x | x | x | x |
| 100 μM | x | x | x | x |
| 200 μM | x | x | x | x |
| 300 μM | x | | x | x |
| 400 μM | x | | | |
| 500 μM | x | | | |
| 1000 μM | | | | |

Figure 2:
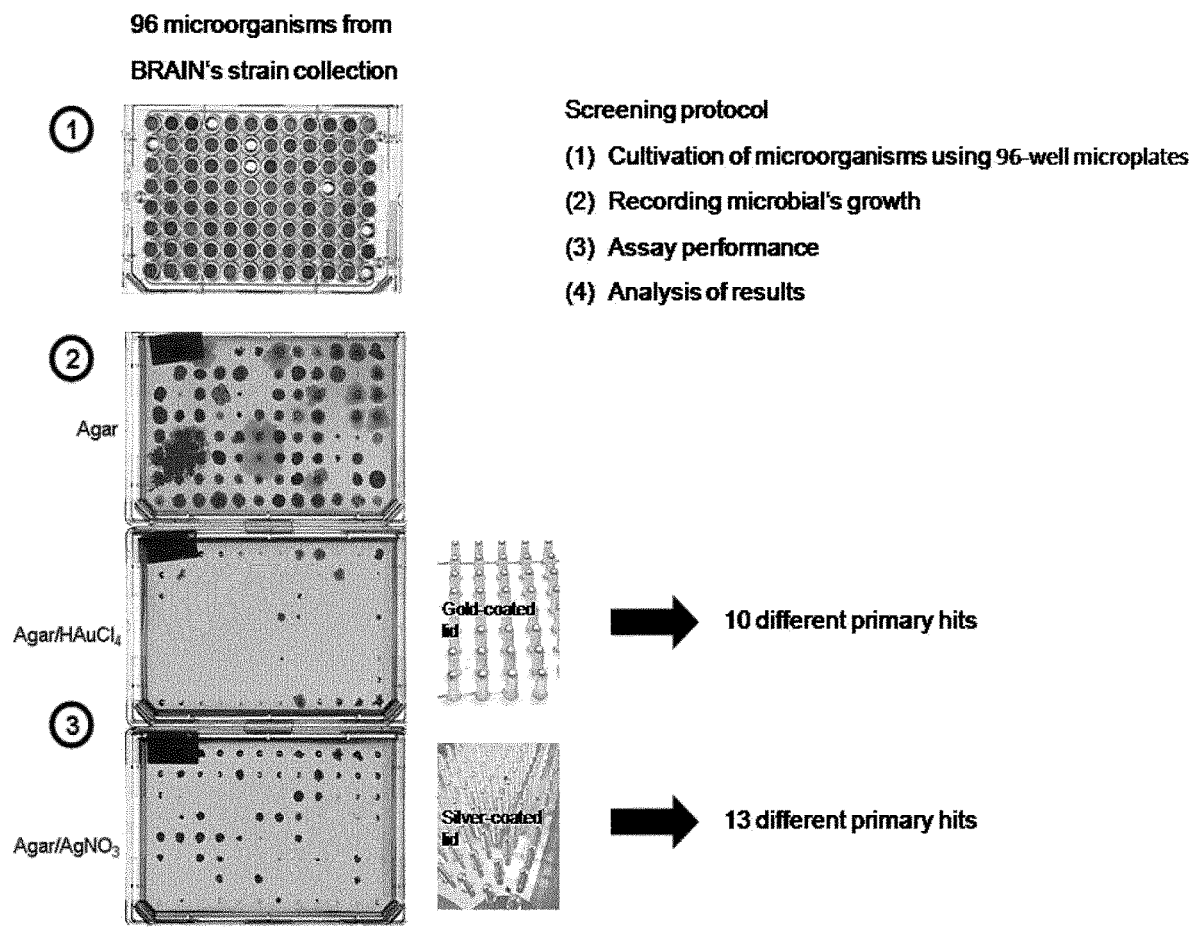
FIG. 2: Screening of microorganisms from a proprietary strain collection (Bioarchive of BRAIN AG) using silver and gold coated pins and subsequent selection on agar medium comprising 200 μM $AgNO_3$ or 400 μM $HAuCl_4$, respectively.

For the discovery of novel microorganisms with resistance to silver and gold, a screening assay was set up using microorganisms from the proprietary strain collection of the BRAIN company of the species indicated in FIG. 2. For this assay, the second selection was carried out in a concentration of 200μM AgNO$_3$ and 400μM HAuCl$_4$, respectively.

The procedure was as follows. First, the organisms were cultivated for 1 to 2 days in 750 μL medium in 96 deep well plates at 300 rpm and 28° C. 100 μl of each of the cultures were transferred into two microplates, each equipped with pins coated with silver or gold, respectively. Incubation was for 3 hours 28° C. at 450 rpm, followed by washing with saline and draining the liquid off on sterile cellulose paper. The cultures were stamped on agar containing 400 μM HAuCl$_4$ or 200 μM AgNO$_3$, respectively, and incubated at 28° C. up to 4 to 6 days (FIG. 2).

Example 3

Biological Separation Process (BSP)

168 metallophilic microorganisms identified in the resistance and binding assay were used for separation experiments according to the following procedure. Microorganisms were streaked out on agar plates directly after thawing (conservation vials are kept at −80° C.) and the plates were cultured at 28° C. overnight. The cultures were inoculated in liquid Luria-Bertani medium and cultured at 28° C. overnight. After that, these pre-cultures were split and inoculated in fresh medium. One of the cultures was induced by the addition of 20 μM AgNO$_3$ or 40 μM HAuCl$_4$, respectively. The other culture was grown under the same conditions without metal ion treatment. Both cultures were incubated at 28° C. over night. The cells were sedimented by centrifugation at 4500 rpm for 10 min, resuspended in 0.9% NaCl and the optical density at 578 nm was determined. Cells were diluted finally to OD5 per 20 ml using 0.9% NaCl.

Figure 3:
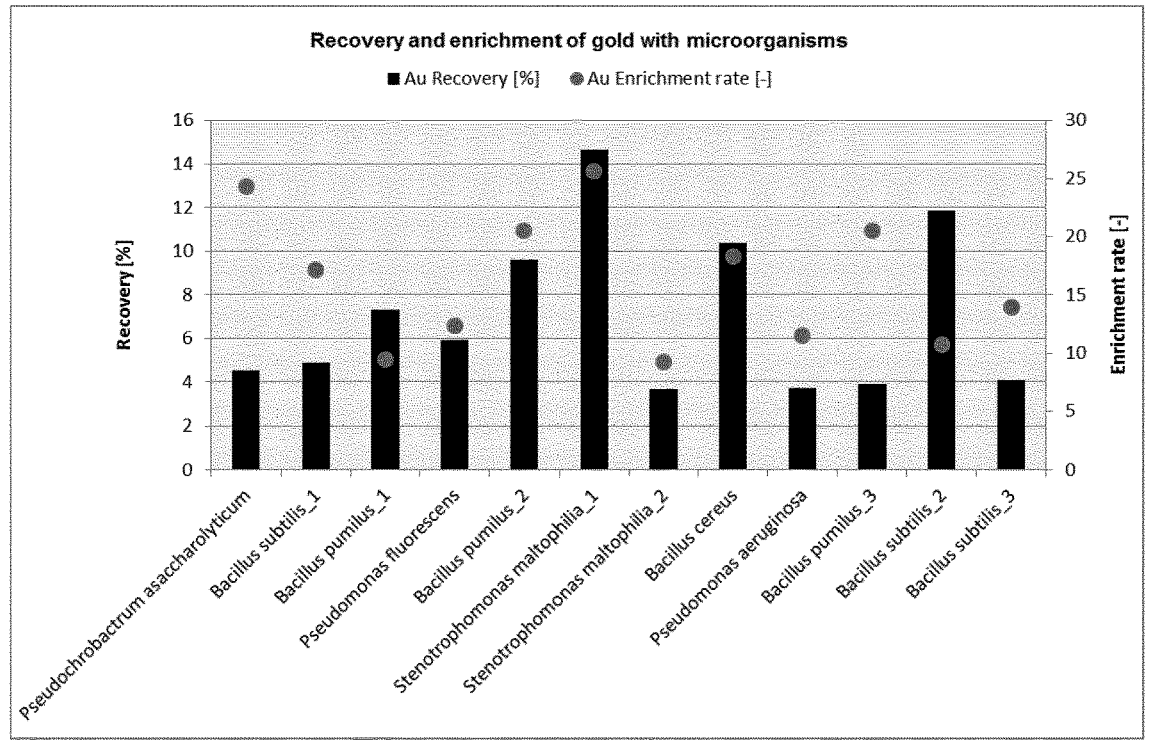
FIG. 3: Selection of the best candidates. 12 microorganisms from 168 were selected due to their resistance to gold- and silver ions and their performance in the biological separation process (BSP). The $1^{st}$ to $4^{th}$ and $6^{th}$ organisms from the left were selected for further upscaling of the process. Recovery [%] ([μg] Au K/([μg] Au E)*100; K=Concentrate (Flotate); E=Total Ore; Enrichment rate [−]: ([μg] Au K/[g] K)/([μg] Au E/[g] E); K=Concentrate (Flotate); E=Total Ore; a) Analysis of gold, b) Analysis of silver.
Figure 3:
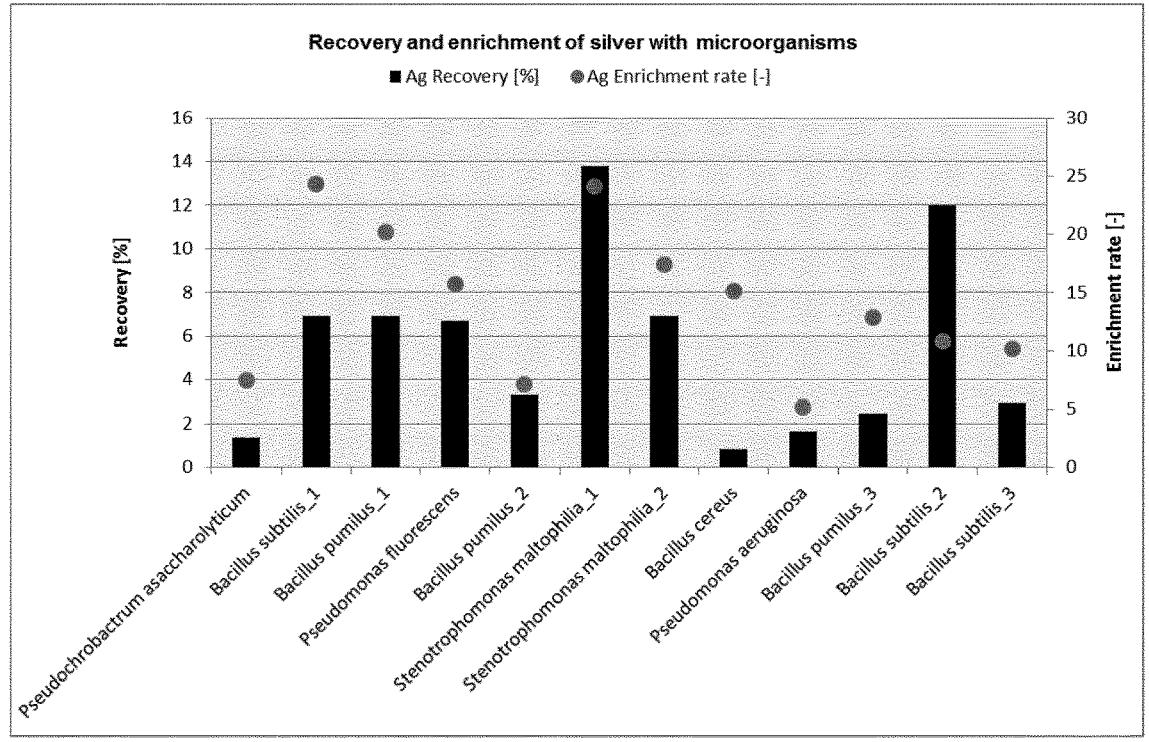

Silver or gold containing ore was sieved and 0.5 g ore was mixed with 20 ml of the cell suspension from the 168 positively screened microorganisms in a 25 ml beaker glass. A cross-shaped magnetic agitator was added, the beaker glass sealed with Parafilm® and the mixture of ore and cell suspension stirred at 100 rpm for 16 hours on a magnetic stirrer. After the agitated incubation time, the mixture was left for 3h at ambient temperature without stirring. The result from the BSP was documented by photography and the film comprising the biomass with bound metal on the surface was removed for further gold and silver analysis via ICP-MS. 12 bacterial species showing the highest bound amounts of gold and silver were selected. The recovery and enrichment rate of gold and silver for these 12 non-induced microorganisms is shown in FIGS. 3a and 3b. The recovery [%] given on the primary vertical axis was determined as follows: ([μg] Au K/[μg] Au E)*100; K=Concentrate (Flotate); E=Total Ore.

The enrichment rate [−] given on the secondary vertical axis was determined as follows: ([μg] Au K/[g] K)/([μg] Au E/[g] E); K=Concentrate (Flotate); E=Total Ore.

Figure 4:
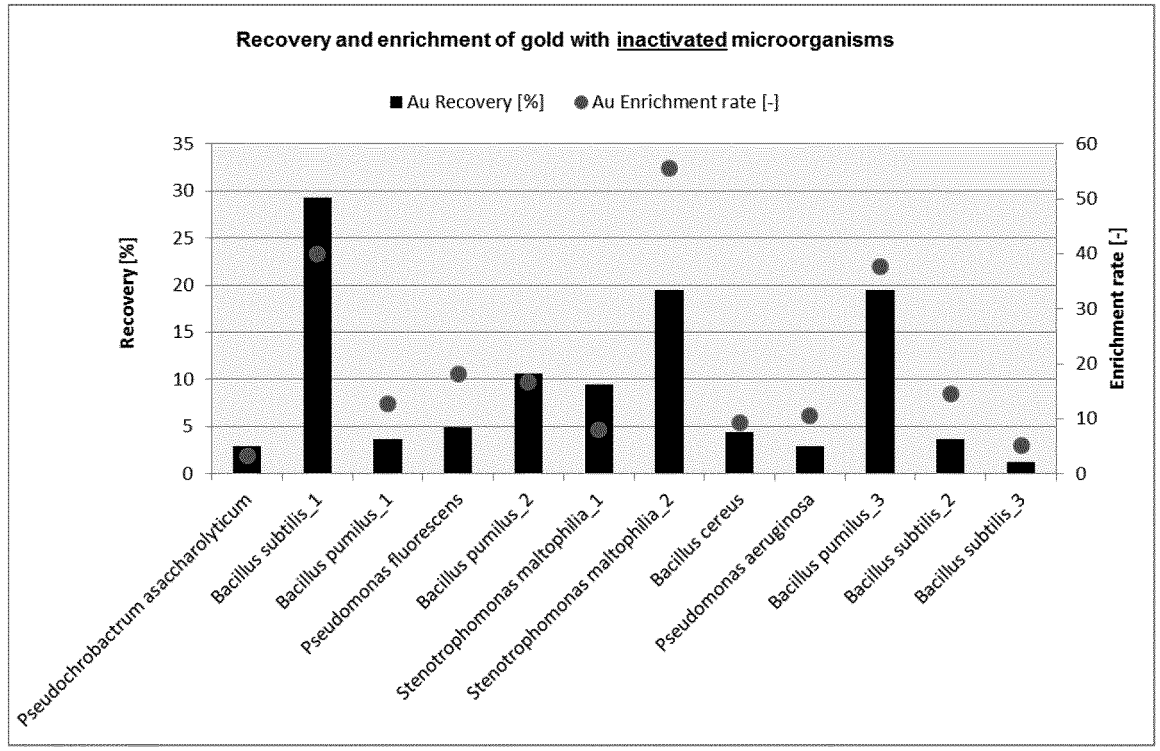
FIG. 4: Inactivated biomass of 12 selected microorganisms and their performance in the biological separation process (BSP). Inactivated biomass was generated by sterilization (121° C., 20min, 1 bar). Recovery [%] ([μg] Au K/([μg] Au E)*100; K=Concentrate (Flotate); E=Total Ore; Enrichment rate [−]: ([μg] Au K/[g] K)/([μg] Au E/[g] E); K=Concentrate (Flotate); E=Total Ore; a) Analysis of gold, b) Analysis of silver.
Figure 4:
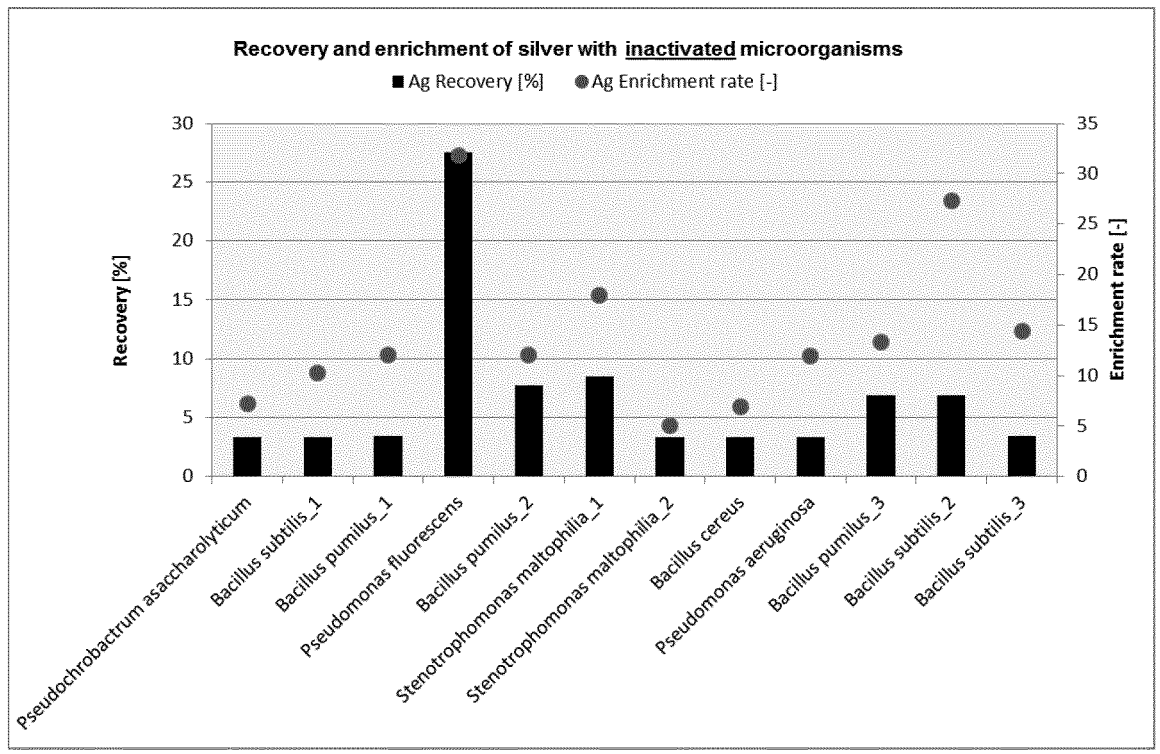

Biological separation was also performed with inactivated biomass. For that, identical process conditions as described above were used. Instead of living microorganisms inactivated biomass was used, which was inactivated at 121° C. for 20 min using 1 bar pressure. The recovery and enrichment of gold and silver for the biomass of the 12 non-induced microorganisms is shown in FIGS. 4a and 4b. Surprisingly, for some organisms the recovery of gold and silver was considerably higher when dead biomass was used as compared to living biomass.

Example 4

Process Parameters for Precious Metal Enrichment from Ore Preparation of Biomass and Determination of Cell Dry Weight Biomass was generated by fermentation under culture conditions as described above. Bacterial cells were harvested and cell dry weight (CDW) was determined. Biomass was sedimented in the culture medium by centrifugation at 4500 rpm for 10 min, washed with 0.9% NaCl and dried on a glass fibre mat at 125° C.

Enrichment of Precious Metals

For the enrichment of the precious metals Au and Ag in the non-soluble, elemental form a ratio of biomass to ore was shown to be optimal in the process of the invention in the range of 0.01 to 20%, more preferred 0.05% to 0.5% (CDW/w. ore). Table 3 shows which microorganisms are best suited for the enrichment of silver and gold from different ores as source.

Combinations of microorganisms have also proven to be advantageous. For the enrichment of gold a combination of e.g. *B. subtilis* (MO1) and *P. fluorescens* (MO2) with biomass ratio of MO1 to MO2 e.g. 80:20, 70:30, 30:70 or 20:80) has shown results which were superior to the use of a biomass of a single microorganism. Combinations of different bacteria for MO1 and MO2, more than two or more than three different bacteria are conceivable. The biomass comprising a mixture of bacterial species is used in the same ratio CDW/w. ore as the biomass comprising a single species.

For ores comprising 0.3-5 ppm (µg/g or g/t) elemental gold enrichment factors of 30 times to 98 times were achieved using the process described herein.

TABLE 3

| Type of ore | Microorganism | Metal |
| --- | --- | --- |
| oxidic | B. subtilis, P. fluorescens | Au, Ag |
| oxidic-transitional | B. subtilis | Au, Ag |
| transitional | B. subtilis, B. pumilus, P. fluorescens, P. aeruginosa | Au, Ag |
| sulfidic | B. subtilis | Au, Ag |

The invention claimed is:

1. A process of isolating or enriching a heavy metal present in a liquid medium, comprising
a step of incubating a suspension containing (i) particulate scrap metal, household waste and/or industrial waste containing a heavy metal in elemental form and (ii) biomass comprising a bacterium, or a combination of two or more bacteria, capable of binding the heavy metal;
a step of separating the biomass having bound heavy metal from the suspension of the previous step; and
a step of isolating the heavy metal from the biomass separated in the previous step;
wherein the heavy metal is selected from ruthenium, rhodium, palladium, silver, osmium, iridium, platinum, gold, and/or rare earth metals; and wherein the bacterium, or the combination of two or more bacteria, is selected from the following species:
*Pseudochrobactrum asaccharolyticum* and *Stenotrophomonas maltophilia*.

2. The process according to claim 1, wherein said suspension contains the scrap metal, household waste and/or industrial waste, in the separating step, in an amount of from 1 to 60% (w/w) based on the total weight of the suspension.

3. The process according to claim 2, wherein said suspension contains the scrap metal, household waste and/or industrial waste in an amount of from 10 to 25% (w/w) based on the total weight of the suspension.

4. The process according to claim 1, wherein said bacterium, or the combination of two or more bacteria, comprises at least one bacterium selected from *Pseudochrobactrum asaccharolyticum* (DSM-25619) and *Stenotrophomonas maltophilia* (DSM-50170).

5. The process according to claim 1, wherein said biomass is or comprises dead biomass.

6. The process according to claim 1, wherein the incubating step comprises agitating the suspension containing the heavy metal and the biomass for forming a film or foam containing biomass having bound heavy metal; and the separating step comprises removing the film or foam from the suspension.

7. The process according to claim 1, wherein the incubation step is conducted in a reactor comprising an agitator for agitating the suspension.

8. The process according to claim 1, wherein said suspension contains, in the separating step, a cell dry weight of said biomass in an amount of from 0.01 to 20% (w/w) based on the weight of the scrap metal, household waste and/or industrial waste contained in the suspension.

9. The process according to claim 8, wherein said suspension contains a cell dry weight of said biomass in an amount of from 0.05 to 0.5% (w/w) based on the weight of the scrap metal, household waste and/or industrial waste contained in the suspension.

10. The process according to claim 1, wherein said step of incubating is conducted for a period of from 0.5 to 16 hours.

11. The process according to claim 1, wherein the heavy metal is silver and/or gold.

12. The process according to claim 1, wherein said heavy metal is a precious metal selected from ruthenium, rhodium, palladium, silver, osmium, iridium, platinum, and/or gold.

13. The process according to claim 1, wherein said scrap metal, household waste and/or industrial waste contains the heavy metal in an amount of at most 10000 ppm by weight.

14. The process according to claim 1, wherein the particulate scrap metal, household waste and/or industrial waste has a particle size of at most 400 µm determined by sieving.

15. The process according to claim 10, wherein said step of incubating is conducted for a period of from 1 to 2 hours.

16. The process according to claim 13, wherein said particulate ore contains the heavy metal in an amount of at most 1000 ppm by weight.

17. The process according to claim 13, wherein said particulate ore contains the heavy metal in an amount of at most 100 ppm by weight.

18. The process according to claim 14, wherein said particulate ore has a particle size of at most 200 µm determined by sieving.

19. The process according to claim 14, wherein said particulate ore has a particle size of at most 100 µm determined by sieving.

* * * * *